United States Patent [19]

Meyer et al.

[11] Patent Number: 4,941,876

[45] Date of Patent: * Jul. 17, 1990

[54] DEVICE FOR CONDITIONING LIQUIDS OR LIQUID AND SOLID SUBSTANCES

[75] Inventors: Gabriel Meyer; Ernst Howald, both of Vesenaz, Switzerland

[73] Assignee: Medicorp Holding S.A., Luxembourg

[*] Notice: The portion of the term of this patent subsequent to Sep. 9, 2003 has been disclaimed.

[21] Appl. No.: 143,078

[22] PCT Filed: Mar. 23, 1987

[86] PCT No.: PCT/EP87/00163

§ 371 Date: Dec. 10, 1987

§ 102(e) Date: Dec. 10, 1987

[87] PCT Pub. No.: WO87/06141

PCT Pub. Date: Oct. 22, 1987

[30] Foreign Application Priority Data

Apr. 10, 1986 [CH] Switzerland .............. 01413/86

[51] Int. Cl.$^5$ .............................................. A61M 5/28
[52] U.S. Cl. ..................................... 604/89; 604/191; 604/238; 604/416; 206/221
[58] Field of Search .............. 604/56, 82, 89–92, 604/218, 231, 236, 238, 416, 191; 215/6; 206/219, 221

[56] References Cited

U.S. PATENT DOCUMENTS

| | | | |
|---|---|---|---|
| 2,549,417 | 8/1949 | Brown | 604/90 |
| 2,576,951 | 12/1951 | Lockhart | 604/90 |
| 3,159,159 | 12/1964 | Cohen | 604/236 |
| 3,467,097 | 9/1969 | Ogle | 604/416 |
| 3,563,415 | 2/1971 | Ogle | 604/231 |
| 3,674,028 | 7/1972 | Ogle | 604/90 |
| 3,881,484 | 5/1975 | Gidcumb, Jr. | 604/89 |
| 4,439,184 | 3/1984 | Wheeler | 604/90 |
| 4,610,669 | 9/1986 | Meyer et al. | 604/218 |
| 4,657,534 | 4/1987 | Beck et al. | 604/231 |
| 4,741,737 | 5/1988 | Meyer et al. | 604/231 |

FOREIGN PATENT DOCUMENTS 1441390 4/1962 Fed. Rep. of Germany ...... 604/236

Primary Examiner—Stephen C. Pellegrino
Assistant Examiner—Ralph Lewis
Attorney, Agent, or Firm—Davis, Bujold & Streck

[57] ABSTRACT

The device comprises a cylindrical ampoule which is closed at one end and opened at the other end. The ampoule has a relatively large circular cylindrical zone adjacent the closed end and a relatively small cylindrical zone disposed between the relatively large cylindrical zone and the open end of the ampoule. A piston valve engages the open end of the ampoule to provide sealing engagement and dispensing of the liquid contents when desired. An intermediary stopper engages the relatively small cylindrical zone, when the stopper is in a storage position, to divide the ampoule into first and second storage compartments. The stopper is shaped to provide tight sealing engagement with the relatively small circular cylindrical zone while providing at least one opening, between its lateral surface and the interior wall of the ampoule, for allowing passage and mixing the substances contained in the compartments, when it is positioned in the relatively large circular cylindrical zone.

11 Claims, 5 Drawing Sheets

Fig. I
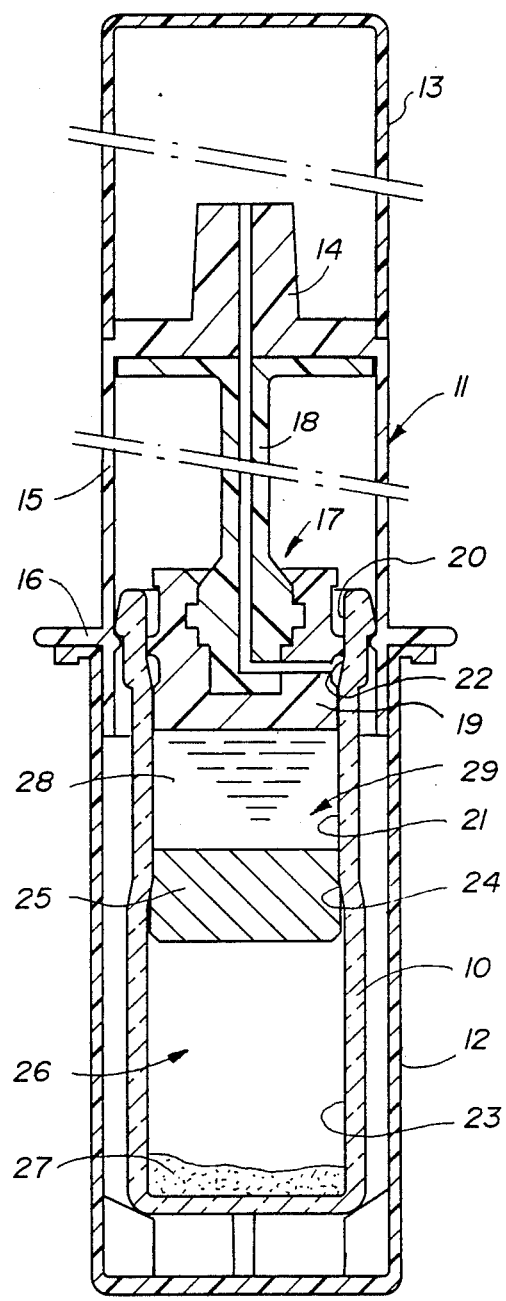
Fig. II
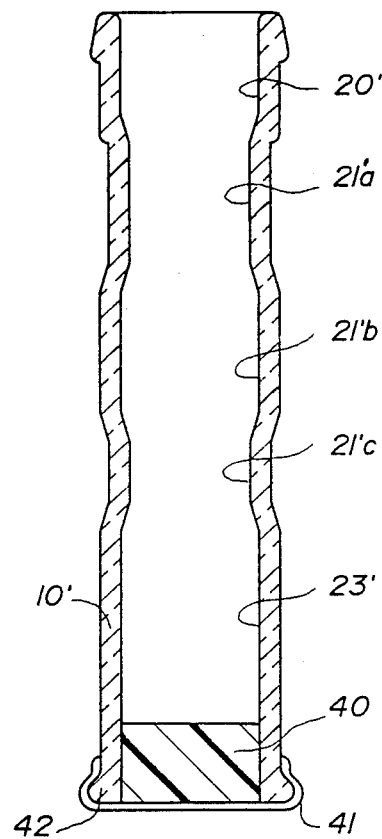

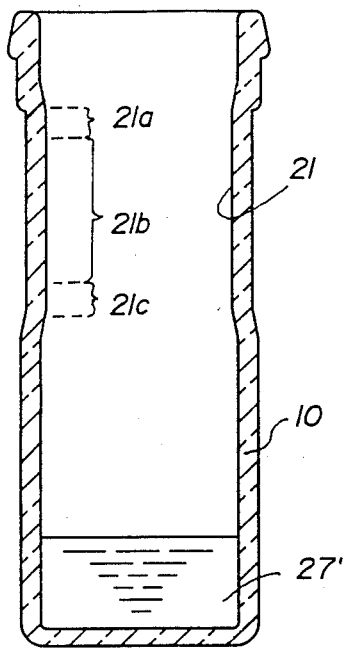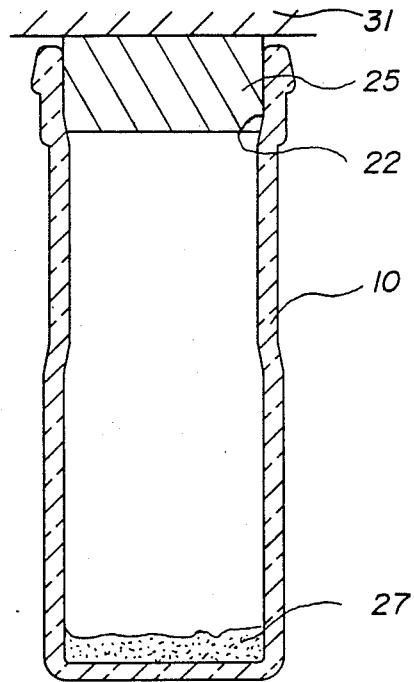
Fig. 2  Fig. 4
Fig. 5  Fig. 6
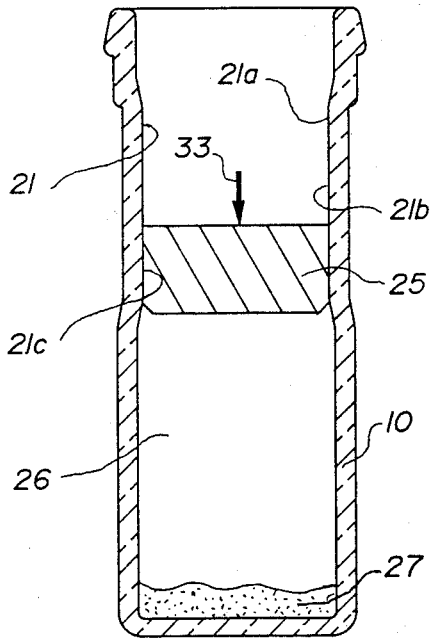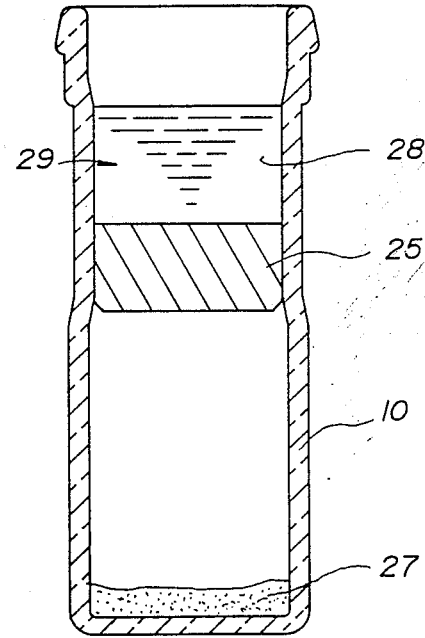

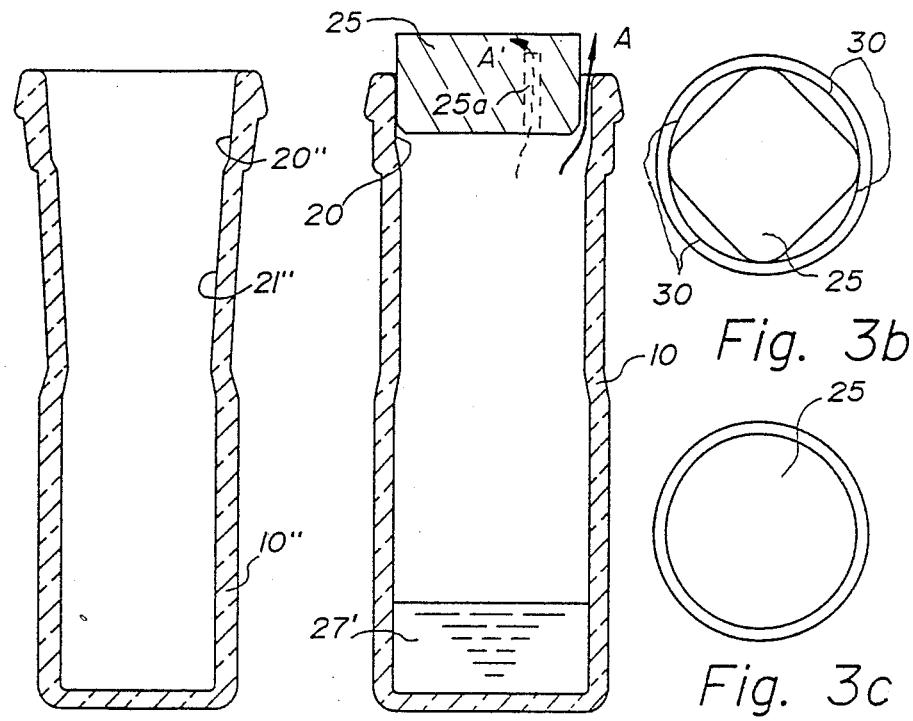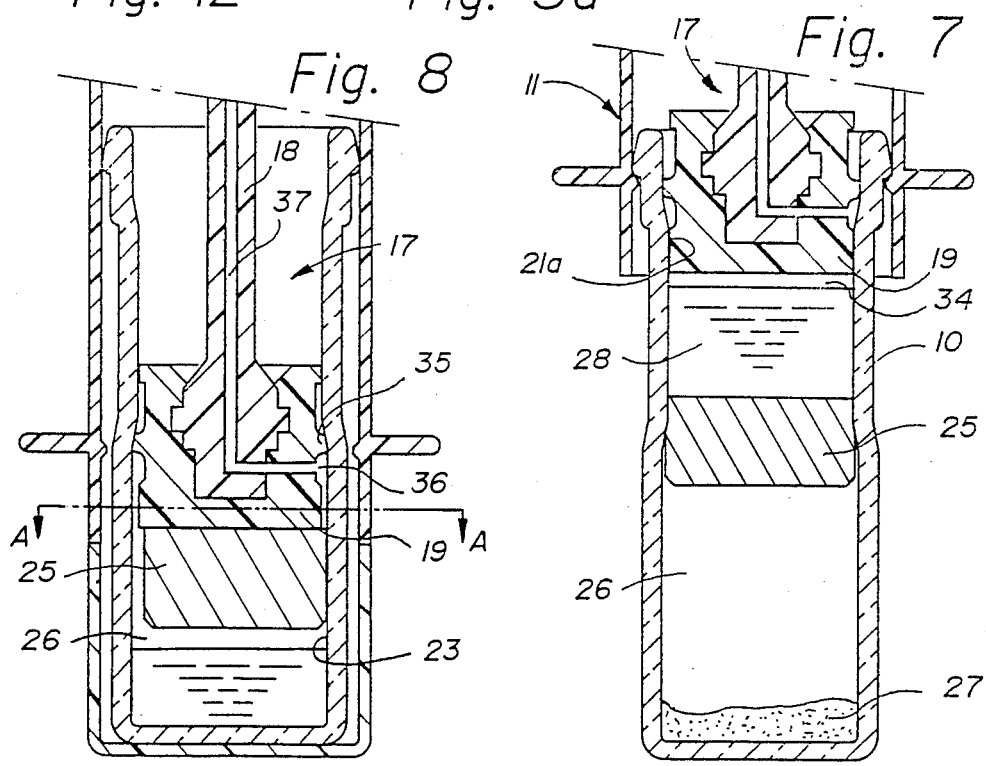

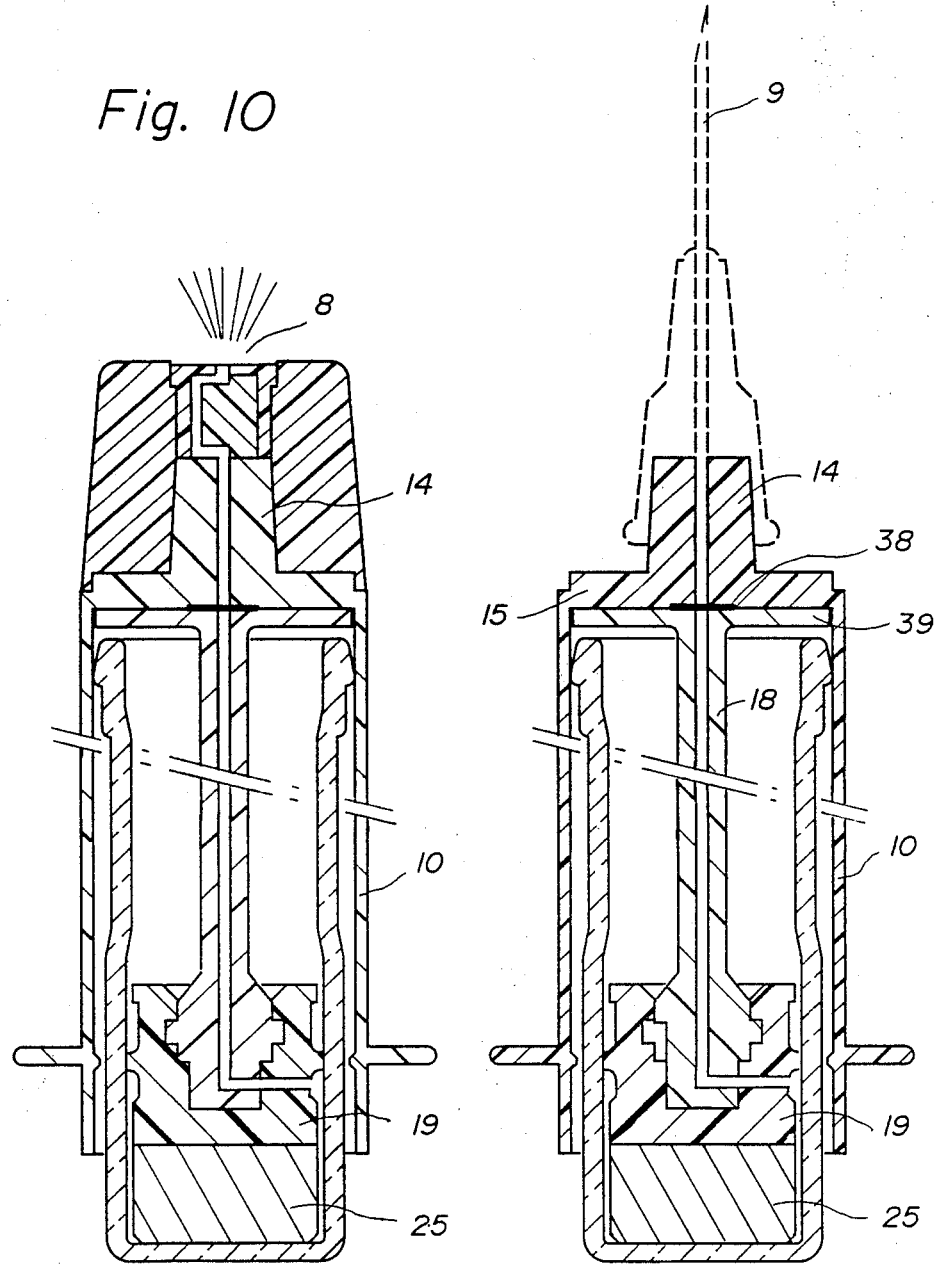

DEVICE FOR CONDITIONING LIQUIDS OR LIQUID AND SOLID SUBSTANCES

The present invention concerns a device for conditioning liquid substances or liquids and solids, comprising a generally cylindrical, elongate ampoule of circular cross-section with two compartments each disposed in the extension of the other and separated by an intermediate moveable elastomeric plug or stopper. Each compartment contains different substances which are separately stored and later mixed together to form a liquid mixture for medical or paramedical purposes. The device is designed initially to provide storage of the different substances and later to insure proper mixing of the substances to form a liquid mixture and to dispense the same from the conditioning device.

The ampoule is closed at one end and open at the other end and comprises at least one cylindrical zone of narrow circular section, tapering to form a smaller area inside the ampoule and at least one cylindrical zone of a wide circular cross-section. During the storage phase, the narrow circular cylindrical section is tightly sealed, at one end, by the movable intermediary elastomeric plug so as to form a first compartment inside the ampoule which is disposed between the closed end of the ampoule and the moveable intermediary plug. The second compartment is disposed between the moveable intermediary plug and the open end of the ampoule, with the open end of the ampoule being closed by a piston-valve. During mixing of the two substances, the moveable intermediary plug is forced from the narrow circular cylindrical zone into the wider circular cylindrical zone to allow communication between the first and second compartments and mixing of the substances contained therein. The narrow circular cylindrical zone remains blocked by the piston valve. During dispensing, the piston valve is forced inside the ampoule to evacuate the liquid mixture from the ampoule.

U.S. Pat. No. 3,563,415 describes a distributor of liquid droplets comprising a vessel with two compartments, one of which contains a powder and the other a liquid solvent. The two substances being designed for mixing into a liquid medication. These two compartments are separated by an intermediary plug held in position in a narrow neck during the storage phase of the distributor. The neck also contains a plug comprising a first element slidable within the neck and having a radial canal, and a second element disposed for adaptation on the first element to block said radial canal. The compartment storing the powder has a considerably larger diameter than the neck. At the time of use, the plug is driven into the neck. The pressure exerted by the liquid solvent in one of the compartments pushes the intermediary plug into the compartment holding the powder. Gravity pulls the intermediary plug into said compartment and mixing can take place. When the powder is completely dissolved by the liquid, the second element of the plug is removed, thereby opening the radial canal and causing the medication to flow.

This device does not lend itself to use as an injection syringe or a spray device. Its only use is as a two compartmented conditioning device, the liquid medication resulting from mixing the two components flowing outside of the container by means of gravity.

European Patent Application Published as No. 0 144 483 describes a syringe of the mixing type, comprising a syringe body which is divided, during the storage phase, into two compartments by means of an intermediary plug. The syringe body is essentially cylindrical and its distal extremity has a needle, while its posterior extremity is closed by a piston head. The syringe body has a lateral deformation approximately towards the center, for example, a convex curved portion defining the trajectory of origin for transferring the liquid from the posterior compartment to the anterior compartment or mixing chamber when the intermediary plug is forced to the top of this curved portion.

When the component in the anterior compartment during the storage phase is a lyophilisate, the original substance to be lyophilized, usually in liquid form, is actually held in a compartment defined at one end by partitions inside the syringe body and at the other end, by one surface of the intermediary plug. To evacuate gases formed during the lyophilization operation, the distal extremity of the syringe remains open while its other end must be tightly sealed by the intermediary plug. Such impermeability is difficult to attain during the lyophilization phase which is known to be accompanied by congealing during which the elastomeric stopper means looses all or some of its elastic properties. One of the disadvantages of the system described arises from the fact that the substance to be lyophilized is of necessity in contact with the glass syringe body and with the elastomer of the intermediary plug during the lyophilization phase, and from the fact that it is difficult to maintain impermeability between these two materials during the congealing which necessarily accompanies lyophilization.

Furthermore, means must be provided to block the distal extremity of the syringe with the needle opening directly into the anterior compartment initially containing the lyophilisate and serving as the mixing chamber.

The present invention proposes to overcome the foregoing disadvantages of the systems known in the art by proposing a double-compartmented conditioning device wherein two substances, respectively contained in two compartments, can be mixed in a sealed environment, and by using said mixture as a substance to be injected with a syringe, as a substance to be sprayed or poured in droplets or in a stream.

Another advantage of the device is that the operations of filling and positioning the various elements can take place automatically in a long series, with the ampoules proceeding side by side unsupported on the transporting means or conveyor belts taking them to different filling and/or assembly stations.

Furthermore, all functions necessary during storage and use, particularly the respective impermeability of the two compartments during storage and the piston effect of ejecting the mixture from the mixing chamber during the usage phase, are accomplished by two elements, that is, a movable intermediary plug and a piston-valve cooperating with an ampoule closed at one end with certain shape specifications. The above results in a greatly simplified manufacture and security of use.

This goal is realized by the conditioning device according to the invention characterized in that the movable intermediary stopper has, in its distended state within the cylindrical zone of wide circular section, a shape other than circular, a smaller surface than the surface of the transverse section of the said zone of wide circular section, and at least one transverse dimension equal to the diameter of the said zone of wide circular section, and by the fact that the movable intermediary plug when in its compressed state within the cylindrical zone of narrow circular section, is circular with a diameter equal to that of the transverse section of said zone.

According to a first embodiment, the ampoule comprises a sole cylindrical zone of narrow circular section disposed near its open end and a sole cylindrical zone of wide circular section disposed near its closed end, said cylindrical zone of narrow circular section essentially comprising the said second compartment and said cylindrical zone of wide circular section essentially comprising the said first compartment.

According to a variation of the first embodiment, the ampoule comprises a unique cylindrical zone of narrow circular section disposed between the first cylindrical zone of wide circular section and a second cylindrical zone of wide circular section, said cylindrical zone of narrow circular section comprising essentially the said second compartment and the second cylindrical zone of wide circular section comprising essentially the said first compartment.

In this variation, the said cylindrical zone of narrow circular section may comprise three sections, the first having a diameter adapted to seal the piston-valve tightly during the storage phase, the second defining the second compartment and the last having a diameter sufficient to seal the movable intermediary plug tightly during the same storage phase.

According to another embodiment the ampoule comprises a first cylindrical zone of wide circular section, a first cylindrical zone of narrow circular section, a second cylindrical zone of wide circular section, a second cylindrical zone of narrow circular section and a third cylindrical zone of wide circular section, the first cylindrical zone of narrow circular section having a diameter adapted to seal the piston-valve tightly during the storage phase and the second cylindrical zone of narrowed circular section having a diameter adapted to seal the movable intermediary plug tightly during the same phase, the said cylindrical zones of wide circular section defining the first and second compartments, respectively.

According to a variation of the above-described device, the first narrow cylindrical zone of circular section is conical, diverging towards the open end of the ampoule.

The movable intermediary plug is preferably more or less cylindrical and its lateral surface is at least approximately polygonal in cross-section when in its distended state.

According to a preferred embodiment, the movable intermediary plug is more or less cylindrical and its lateral surface is approximately oval in cross-section when in its distended state.

The same specifications may also be applied to the stopper means, which may have a generally cylindrical shape and a lateral surface of an approximately polygonal shape in its distended state or an approximately oval shape in the same state.

To facilitate evacuation of vapors during the lyophilization operation, the movable intermediary plug may have a slit in part of its top, said slit opening onto the surface facing the base of the ampoule.

The present invention will be better understood with reference to the description of one example of an embodiment and to the attached drawings, in which:

FIG. 1 shows an axial cross section of the conditioning device according to the invention in its storage position.

FIG. 2 shows the first stage of filling the ampoule.

FIG. 3A is an axial cross-section showing the second manufacturing stage of the device, more particularly, when one of the conditioned substances undergoes lyophilization.

FIGS. 3B and 3C are top plan views of the ampoule as shown in FIG. 3A.

FIG. 3D is a plan view of a second shape of the intermediate stopper in the large cylindrical zone.

FIGS. 3E and 3F are cross-sectional views, along section line A—A of FIG. 8, showing two shapes of the stopper means of the piston-valve when positioned in the large cylindrical zone.

FIG. 4 shows a later phase of filling the ampoule, after lyophilization of one of the substances contained therein.

FIG. 5 shows the phase of positioning the movable intermediary plug after filling the first ampoule compartment.

FIG. 6 shows the stage of filling the second ampoule compartment.

FIG. 7 shows positioning of the injector.

FIG. 8 is a partial longitudinal cross section showing the utilization stage of the conditioning device after mixing the two substances respectively contained in the two ampoule compartments.

FIG. 9 shows the conditioning device used as an injection syringe.

FIG. 10 shows the conditioning device used as a spraying device.

FIG. 11 shows an axial cross section of another embodiment of the conditioning device according to the invention, and FIG. 12 shows an axial cross section of another embodiment of the conditioning device illustrated in FIGS. 1 through 10.

With reference to FIGS. 1 through 10, the double-compartment conditioning device for medical or paramedical use as previously described in detail essentially comprises a generally cylindrical ampoule 10, an injector 11 connected to said ampoule, an ampoule cover 12 coupled with injector 11 and covering essentially the entire ampoule, and a tip cover 13, also coupled with injector 11, designed to protect a tip 14 integral with one end of injector 11. Depending upon which embodiment is chosen, the injection tip may have a needle 9, as shown in more detail in FIG. 9, and the conditioning device then becomes a prefilled mixing syringe; or a spray nozzle 8, as shown more particularly by FIG. 10, and the conditioning device then becomes a nasal spray device or a droplet-measuring device or a pouring device, etc.

Injector 11 includes a capsule 15 comprising a cylindrical sleeve closed at one end by a base connected to the needle-holding tip 14 and open at its opposite end which encases the open end of ampoule. Said open end of capsule 15 has two flanges 16 used in known manner at the moment of injection. The injector further includes a piston-valve 17 mounted inside capsule 15 and attached to its base, for example by means of microwave soldering. Said piston-valve consists of a piston shaft 18 supporting a stopper means 19 which serves as the piston head in certain phases of use to be described later in more detail.

Ampoule 10, closed at one of its extremities, comprises near its open extremity a first cylindrical zone of wide circular section 20 followed by cylindrical zone 21 of narrow circular section connected to preceding zone 20 by a first truncated connecting zone 22. The cylindrical zone of narrow circular section 21 is followed by a second cylindrical zone of wide circular section 23 connected to the preceding zone by a second truncated connecting zone 24.

In the storage position illustrated in FIG. 1, a movable intermediary plug 25 is partially engaged within the cylindrical zone of narrow section, near the second truncated connecting zone 24. Stopper means 19 of piston-valve 17 is partially engaged within said cylindrical zone of narrow circular section 21 near the first truncated connecting zone 22. Thus, movable intermediary plug 25 defines, along with the ampoule base, a first compartment 26, hereinafter called the mixing chamber, which holds a lyophilisate 27 during storage or any other substance to be mixed with a second substance 28, for example a liquid solvent held during storage in a second compartment 29 disposed between the movable intermediary plug 25 and stopper means 19. During the entire storage stage, the two compartments are tightly sealed from each other by movable intermediary plug 25 and the substances therein are mutually isolated.

FIGS. 2 through 8 show the different filling and assembly stages resulting in the double compartmented conditioning device as shown in the storage position of FIG. 1.

In the example shown, ampoule 10 is first filled with a liquid substance 27' which, following lyophilisation in known manner, will be transformed into lyophilisate 27 held in mixing chamber 26 of the ampoule. The cylindrical zone of narrow circular section 21 preferably comprises three sections 21a, 21b and 21c. Section 21a is called the storage section and it is sealed by stopper means 19. Its diameter is defined so as to ensure impermeability of the said stopper means 19 during the storage phase of the conditioning device. Section 21c is called the storage section and it is sealed by movable intermediary plug 25. Its diameter is defined so as to ensure that it is sealed by the said stopper during the entire storage phase, said seal being tight enought to totally isolate the substances respectively held in the two compartments. Central section 21b is an intermediary section between the two storage sections. Its diameter may be equal to that of the two storage sections 21a and 21c, but this is not obligatory. The only necessary condition is that the piston-valve remain sealed during its entire displacement phase through the cylindrical zone of narrow circular section, that is, through the three sections 21a, 21b and 21c. The diameter of intermediary section 21b may be somewhat larger than that of sections 21a and 21c, so as to exert less force on stopper means 19 in this section, but in no case may this diameter exceed the limit which would cause the piston-valve seal to fail.

As previously mentioned, movable intermediary plug 25 is partially engaged within the second truncated connecting zone 24 during the storage phase. In this zone, the corresponding portion of the plug is less compressed than the portion engaged in the cylindrical zone 21 of narrowed circular section, and is poised to assume its original shape rapidly when movable intermediary plug 25 is later forced into the wide circular cylindrical zone. As will be seen from the following description of how the system functions, it is indispensable that at least the portion of the movable intermediary plug oriented towards the mixing chamber exerts sufficient friction against the ampoule walls to retain the movable intermediary stopper means in position in the chamber during the transfer phase of the liquid solvent 28 from the second compartment 29 into the mixing chamber. This retention by means of friction is facilitated because the movable intermediary plug does not lose its retentivity despite lengthy storage, and the stopper, or at least a portion of it, can quickly return to its partially distended state.

The same problem arises with the piston-valve and is resolved in the following manner: only stopper means 19 is engaged in a high compression area, the peripheral spline disposed beneath the radial canal (hereinafter described in more detail) being situated in a lower compression area, more specifically, the first cylindrical zone of wide circular section 20 or the first truncated connecting zone 22.

FIG. 3A shows prepositioning of movable intermediary plug 25 prior to the lyophilization phase. FIG. 3B shows a top plan view of movable intermediary plug 25 positioned in the first cylindrical zone 20 of wide circular section. FIG. 3C shows the plug in place in the cylindrical zone of narrow circular section 21 of ampoule 10. The plug is made of elastomeric material and is consequently deformable when force is exerted upon it. In its distended state, its cross section becomes polygonal, perhaps square, so that spaces 30 are formed between the lateral wall of the plug and the interior wall of the ampoule when said plug is engaged in the first cylindrical zone of wide circular section 20 of ampoule 10. However, the shape of the movable intermediary plug need not necessarily be polygonal. Initially, i.e., in its distended state, it may be oval or elliptical, with its wider diameter at least slightly larger than the diameter of the first cylinder of wide circular section 20, and its narrower diameter being considerably smaller than that diameter. In its compressed state, i.e. when it is engaged in cylindrical zone 21 of narrow circular section, the plug deforms into a circular shape having a diameter equal to that of the narrow section cylindrical portion, as is more particularly shown in FIG. 3C. It is tight enough to ensure impermeability.

The openings are used to allow vapors to escape in the direction of arrow A during the lyophilization operation to which the liquid substance 27' is subjected. For this reason, the movable intermediary plug may have a notch or aperture 25a to aid with the evacuation of vapors in the direction of arrow A' during lyophilization.

As is shown in FIG. 4, at the end of this opertion, when original substance 27' has been transformed into lyophilisate 27, intermediary movable plug 25 is thrust deeply enough into ampoule 10 that its anterior extremity penetrates the first truncated connecting zone 22 and tightly seals the ampoule. The movable intermediary plug is first thrust inwardly by means of an upward push exerted on the ampoule body, intermediary plug 25 being in contact with the upper wall 31 of the enclosure of the lyophilization zone, or by means of a downward push exerted by said upper wall 31, or a movable plate disposed within the enclosure of the lyophilization zone. Means may be provided for creating a partial vacuum in the lyophilization enclosure at the end of this operation so that a vacuum also exists within ampoule 10. From the moment that movable intermediary plug 25 is thrust into the ampoule neck sealing it tightly, the partial vacuum will subsist within the ampoule, that is, above lyophilisate 27. However, this condition is not necessary and a controlled atmosphere may exist above the lyophilisate, such as an atmosphere of neutral gas.

During a complementary phase shown in FIG. 5, movable intermediary plug 25 is moved, possibly by mechanical means represented schematically by arrow 33, to the area near the lower extremity of the circular cylinder of narrow cross section 21. Mechanical elements 33 are necessary in some cases, but superfluous in others. Actually, when atmospheric pressure is re-established following the lyophilization phase, if the necessary partial vacuum exists in compartment 26, i.e., above lyophilisate 27, the pressure differential may possibly cause intermediary plug 25 to slide through intermediary section 21b without outside help and become blocked in position in sealed storage section 21c.

FIG. 6 illustrates the next phase which consists of introducing a liquid solvent 28 into upper compartment 29 to be mixed with lyophilisate 27 to reconstitute the medication for injection or absorption, as for example in the case of a spray, by the patient.

The next step, shown in FIG. 7, consists of mounting the injector 11 on ampoule 10 by engaging stopper means 19 of piston-valve 17 within the ampoule neck as far as section 21a of the cylindrical zone of narrow circular section 21. According to a preferred embodiment, filling upper chamber 29 by means of solvent 28 takes place in an atmosphere of carbonic anhydride, a certain amount of which is initially trapped between stopper means 19 and the upper surface of said liquid 28. The volume 34 of the carbonic anhydride dissolves rapidly in liquid solvent 28, thereby creating a depression and causing corresponding upward recovery of equal volume in movable intermediary plug 25. The final result is shown in FIG. 1 and corresponds to the storage position of the conditioning device.

At the time of use, ampoule cover 12 is retracted and replaced by tip cover 13. The latter is dimensioned so that this is done by pressing its flat base while holding the syringe by flanges 16 to progressively position the ampoule as shown in FIG. 8. This movement causes piston-valve 17 to be displaced towards the inside of the cylindrical zone of narrow circular section 21. The movable intermediary plug is pushed from this zone by the pressure integrally transmitted through liquid 28 and penetrates the entry zone of the mixing chamber where it expands and assumes its original shape shown in FIG. 3B, that is, the shape which forms openings 30 between its lateral surface and the interior ampoule walls. Friction forces between the movable intermediary plug and the ampoule tend to maintain the plug in position, while the pressure exerted by the liquid would tend to force it forward into the mixing chamber. The dimensions of the movable intermediary plug and of the openings are preferably determined so that friction is the stronger force, and as a result the movable intermediary plug 25 remains in place and the liquid is transferred from the second compartment into the mixing chamber through openings 30. Thus, movable intermediary plug 25 remains in this position until all the liquid has been transferred and until stopper means 19 comes into contact with its upper surface. Liquid solvent 28 dissolves the lyophilisate in mixing chamber 26. The solution obtained is the medication to be injected, sprayed, or dispensed in droplet or stream form.

Following the first stage during which the movable intermediary plug is blocked and the piston-valve passes through the cylindrical zone of narrow circular section to force the liquid from the second compartment through openings 30, the piston-valve/movable intermediary plug unit proceeds to progressively lodge in the mixing chamber.

In the manner described in applicants' previous patents, piston-valve 17 comprises at least one peripheral flange 35 which, in its distended state, has a slightly larger diameter than that of the second cylindrical zone of wide circular section 23 to force the medication through a radial conduit 36 disposed in stopper means 19 and connected to axial conduit 37 penetrating the shaft of piston 18 to connect with a needle 9 (see FIG. 9), a spray attachment 8 (see FIG. 10) or other device for dispensing the medication. When the user pushes down on the ampoule in the direction of the flanges thereon, the mixture is forced towards the radial canal through openings 30.

In the final stage, intermediary plug 25 is pushed back to the base of ampoule 10 and stopper means 19 contacts the surface of said movable intermediary plug. Obviously, the shape and size of the movable intermediary stopper must be such that the plug can slide axially without bumping inside the ampoule.

As also described in applicants' prior patents, a filter 38 may be interposed between a shoulder 39 supporting the shaft of piston 18 and the base of capsule 15.

For technical reasons, it is difficult to make a relatively long neck of narrow circular cross section. In this case, the narrow cylindrical zone 21 of the preceding example, comprising three only slightly differentiated sections 21a, 21b and 21c, may be replaced by three specifically defined areas. This embodiment is shown in FIG. 11. Ampoule 10', closed at one end, comprises near its open end a first cylindrical zone of wide circular section 20' followed in succession by a first cylindrical zone of narrow circular section 21'a, a second cylindrical zone of wide circular section 21'b, a second cylindrical zone of narrow circular section 21'c, and a third cylindrical zone of wide circular section 23'.

Regarding function, the first cylindrical zone of narrow circular section 21'a corresponds to portion 21'a of cylindrical zone of narrowed circular section 21 in ampoule 10; the second cylindrical zone of narrow circular section 21'c corresponds to portion 21c of cylindrical zone of narrow circular section 21 in ampoule 10; and the second cylindrical zone of wide circular section 21'b corresponds to intermediary portion 21b of cylindrical zone of narrowed circular section 21 in ampoule 10.

In this case, the intermediary stopper is prepositioned in the second cylindrical zone of wide circular section 21'b during the lyophilization phase, thereby allowing vapors to escape through the openings formed by the elastic deformation of the stopper, as previously described.

Throughout the storage period, the stopper means of the piston-valve is positioned in the first cylindrical zone of narrow circular section 21'a and the intermediary plug is in place in the second cylindrical zone of narrow circular section 21'c. The diameters of cylindrical zones of wide circular section 21'b and 23' are such that the piston-valve, and more particularly the one or more annular flanges disposed above the radial canal, fulfill their role of "piston segments" or "scrapers" in elastic contact with the interior walls of the ampoule, and prevent any of the liquid for injection from escaping.

As before, the intermediary plug is made of elastomer and is polygonal, elliptical, regular or irregular, symmetrical or asymmetrical and forms gaps or openings when in place in the cylindrical zones of wide circular section, and forms a perfect seal when in place in the cylindrical zone of narrow circular section. In practice, it may also have a slit or central opening tending to open or close depending upon whether it is in one or the other of the cylindrical zones described.

FIG. 12 shows a variation of the ampoule 10″ comprising in this case a sole cylindrical zone of narrow circular section 21″ slightly conical in shape. This embodiment may be advantageous by facilitating the formation of a glass tube during glass manufacture and additionally by reinforcing compression of the movable intermediary stopper during the storage phase.

The design characteristics of the movable intermediary plug are also applicable to the piston-valve stopper means. Actually, a polygonal, elliptical or other shape, with a variable surface depending upon whether the means is located in a cylindrical zone of narrow circular section or a cylindrical zone of wide circular section, would consequently reduce dead space in the system and decrease problems of diameter tolerance in the mixing chamber. While not obligatory, this embodiment guarantees reliable functioning of the piston-valve under all tolerable manufacturing conditions.

When one of the substances is a lyophilisate, the ampoule preferably comprises a closed base formed of one piece with the body, preferably glass. When one substance is a very fine powder, the ampoule preferably comprises a base closed by a stopper 40 (see FIG. 11) attached by a crimping means 41 adapted on an outwardly-beveled annular portion 42 connected to the corresponding extremity of the ampoule. In this case filling the first compartment with very fine powder would necessarily cause a powder deposit to form along the ampoule walls, thereby hindering the sealing capacity of the movable intermediary stopper. Furthermore, positioning the movable intermediary plug when powder has already been introduced into the ampoule would stir up part of the powder deposited in the base and would also risk hindering the sealing capacity of the said movable intermediate plug. This is why it is advantageous, in this instance, to first position the movable intermediate plug, then stopper means 40 which is then definitively attached by crimping, given the fact that it plays no further role in the functioning of the system.

In all the preceding embodiments, the utilization phase comprises two successive stages: during a first step, the liquid component passes from the second compartment into the mixing chamber which is actually the compartment farthest from the open end of the ampoule, and during a second step the liquid mixture passes from the first compartment through the openings in the movable intermediary plug to be evacuated through the sole orifice in the ampoule. Consequently, a two-fold transfer through the movable intermediary plug is observed, said two-fold transfer being permitted by the specific geometry of the intermediary stopper in combination with the specific geometry of the ampoule.

The resulting advantages are as follows:
1. The system comprises only two active stopper means.
2. The ampoule comprises a sole orifice during use.
3. There is no need to turn over the device during any of the conditioning phases.
4. Mixture of the two components takes place in a completely closed environment.

We claim:
1. A storing, mixing and dispensing device comprising:

(a) a generally cylindrical elongate ampoule (10) having an open one end and a closed end with a cylindrical zone of relatively large circular cross-section (23) disposed adjacent said closed end and a cylindrical zone of relatively small circular cross-section (21) disposed between said cylindrical zone of relatively large circular cross-section and said open end;

(b) an elastic intermediary stopper (25) slidably movable inside said ampoule, said intermediary stopper, when in a storage position, being sealed in at least a portion of said cylindrical zone of relatively small circular cross-section (21) thereby dividing said ampoule into a first compartment, for containing a first substance, disposed between said closed end and said intermediary stopper and a second compartment, for containing a second substance, disposed between said intermediary stopper and said open end;

said intermediary stopper (25) being shaped to have at least one traverse dimension at least equal to the diameter of said cylindrical zone of relatively large circular cross-section, when in a distended state, and defining, when in said cylindrical zone of relatively large circular cross-section, at least one opening (30) extending past the peripheral surface of said intermediary stopper to interconnect the said first and second compartments;

(c) a piston-valve (17) comprising an axially aligned piston flange (35) and stopper means (19), said stopper means being arranged to engage said cylindrical zone of relatively small circular cross-section to seal the open end of the second compartment when in a storage position of the piston-valve (17), and conduit means, for dispensing substances from said ampoule, located within and extending through said piston-valve (17) and communicating with a peripheral surface of said piston-valve between said piston flange and stopper means, said piston flange (35) being in continuous sealing contact with the interior wall of said ampoule at all times while said stopper means (19) providing sealing contact with the interior wall of the ampoule (10) only when engaged with said cylindrical zone of relatively small circular cross-section so that when said stopper means (19) is positioned in said cylindrical zone of relatively large circular cross-section mixed substances can flow past said stopper means into said conduit means for dispensing;

wherein when mixing and dispensing of the first and second substances is desired, said piston-valve is moved from its storage position towards said closed end to force said intermediary stopper (25) into said cylindrical zone of relatively large circular cross-section thereby allowing communication and mixing of the substances contained in the first and second compartments, further movement of said piston-valve (17) toward said closed end moves the stopper means into said cylindrical zone of relatively large circular cross-section whereby the piston flange (35) can force the mixed substances out of the ampoule past said stopper means into and through said conduit means.

2. A device according to claim 1, characterized in that the ampoule (10) comprises a single said cylindrical zone of relatively small circular cross-section (21) and a single said cylindrical zone relatively large circular cross-section (23), said cylindrical zone of relatively small circular cross-section (21) essentially comprising the said second compartment (29) and said cylindrical zone of relatively large circular cross-section essentially comprising the said first compartment (26).

3. A device according to claim 2, wherein said cylindrical zone of relatively small circular section (21) comprises three sections (21a, 21b, 21c), a first section (21a) located adjacent said open end and having a diameter adapted to ensure tight sealing of the piston-valve stopper means (19) when in its storage position, a third section (21c) located adjacent said cylindrical zone of relative large circular cross-section (23) and having a diameter adapted to ensure complete sealing of said intermediary stopper (25), when in its storage position, and a second section (21b) located between said first and third sections and defining the said second compartment (29).

4. A device according to claim 1, wherein the ampoule (10) comprises a single said cylindrical zone of relatively small circular cross-section (21) disposed between first and second cylindrical zones of relatively large circular cross-section (20,23) the first of which is located adjacent said open end and the second of which is said cylindrical zone of relatively large circular cross-section (23) located adjacent said closed end, said cylindrical zone of relatively small circular cross-section essentially comprising the said second compartment (29) and said second cylindrical zone of relatively large circular cross-section essentially comprising the said first compartment (26).

5. A device according to claim 1, wherein the ampoule (10') comprises first, second and third cylindrical zones of relatively large circular cross-section (20', 21'b, 23'), the first of which is disposed near said open end, the third of which is said cylindrical zone of relatively large circular cross-section (23') disposed near said closed end and the second of which is disposed therebetween, and further comprising first and second cylindrical zones of relatively small circular cross-section section (21'a, 21'c), the first of which is a cylindrical zone of relatively small circular cross-section disposed between the first and the second cylindrical zones of relatively large cross-section (20', 21'b) and the second of which is disposed between the second and third cylindrical zones of relatively large cross-section (21'b, 23') and is said cylindrical zone of relatively small circular cross-section, the first cylindrical zone of relatively small circular cross-section (21'a) having a diameter adapted to ensure tight sealing of the piston-valve stopper means (19), when in its storage position, and the second cylindrical zone of relatively small circular section (21'c) having a diameter adapted to ensure tight sealing of said intermediary stopper (25), when in its storage position, the second and third cylindrical zones of relatively large circular cross-section (21'b and 23'), respectively, defining the said first and the said second compartments.

6. A device according to claim 1, wherein said first cylindrical zone of relatively small circular cross-section (21, 21'a, 21'') is conical and diverges in the direction of said open end of the ampoule (10).

7. A device according to claim 1, wherein said intermediary stopper (25) is of generally cylindrical shape and its peripheral surface has an approximately polygonal cross-section in a distended state.

8. A device according to claim 7, wherein the intermediary stopper (25) has an opening formed therein for allowing vapors to escape from said ampoule (10) when said intermediary stopper (25) partially engages said open end.

9. A device according to claim 1, wherein said intermediary stopper (25) is of generally cylindrical shape and its peripheral surface has an approximately oval cross-section in a distended state.

10. A device according to claim 1, wherein said stopper means (19) has a generally cylindrical shape and its peripheral surface has an approximately polygonal cross-section in a distended state.

11. A device according to claim 1, wherein said stopper means (19) has a generally cylindrical shape and its peripheral surface has an approximately oval cross-section in a distended state.

* * * * *